(12) United States Patent
Senn-Bilfinger et al.

(10) Patent No.: US 6,696,461 B2
(45) Date of Patent: Feb. 24, 2004

(54) TRICYCLIC IMIDAZOPYRIDINES

(75) Inventors: Jörg Senn-Bilfinger, Constance (DE); Wilm Buhr, Constance (DE); Reinhard Huber, Allensbach (DE); Ernst Sturm, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/182,654

(22) PCT Filed: Mar. 29, 2001

(86) PCT No.: PCT/EP01/03603

§ 371 (c)(1),
(2), (4) Date: Oct. 4, 2002

(87) PCT Pub. No.: WO01/72757

PCT Pub. Date: Oct. 4, 2001

(65) Prior Publication Data

US 2003/0139412 A1 Jul. 24, 2003

(30) Foreign Application Priority Data

Mar. 29, 2000 (EP) .............................. 00106688
May 26, 2000 (DE) ........................ 100 26 287
Aug. 14, 2000 (DE) ........................ 100 39 689

(51) Int. Cl.[7] .................. A61K 31/4375; A61K 31/437; C07D 471/14; C07D 491/147; A61P 1/04
(52) U.S. Cl. ...................... 514/293; 514/233.2; 546/82; 546/83; 546/65; 544/126
(58) Field of Search .................. 546/82, 83, 65; 544/126; 514/293, 233.2

(56) References Cited

U.S. PATENT DOCUMENTS 4,468,400 A    8/1984  Gold et al.
6,160,119 A  * 12/2000  Senn-Bilfinger ............. 546/83
6,197,783 B1 *  3/2001  Senn-Bilfinger et al. .... 514/293
6,436,953 B1 *  8/2002  Senn-Bilfinger ........... 514/293

FOREIGN PATENT DOCUMENTS

WO    WO 95/27714    10/1995
WO    WO 98/42707    10/1998
WO    WO 98/54188    12/1998

OTHER PUBLICATIONS

Bundgaard H. Design of Prodrugs. (1985) Elsevier. Amsterdam–New York–Oxford. pp. 1–3.*

* cited by examiner

*Primary Examiner*—Evelyn Mei Huang
(74) *Attorney, Agent, or Firm*—Gary M. Nath; Todd L. Juneau; Sheldon M. McGee

(57) ABSTRACT

Compounds of formula (I) in which the substituents as defined in the description are useful for preventing and treating gastrointestinal disorders.

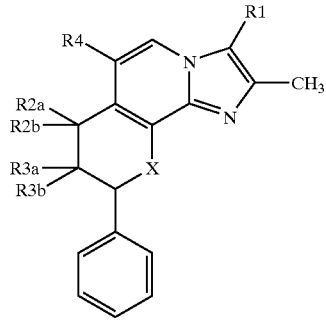

(1)

8 Claims, No Drawings

TRICYCLIC IMIDAZOPYRIDINES

This is a 371 of PCT/EP01/03514, filed on Mar. 28, 2001, which claims the priority of EP 0010669.0, filed on Mar. 29, 2000; DE 10026287.2, filed on May 26, 2000; and DE 10039689.5, filed on Aug. 14, 2000.

FIELD OF APPLICATION OF THE INVENTION

The invention relates to novel compounds which are used in the pharmaceutical industry as active compounds for preparing medicaments.

PRIOR ART

U.S. Pat. No. 4,468,400 describes tricyclic imidazo[1,2-a]pyridines having different ring systems fused to the imidazopyridine skeleton, which compounds are said to be suitable for treating peptic ulcer disorders. The international Patent Application WO95/27714 describes certain 8,9-dihydropyrano[2,3-c]imidazo[1,2-a]pyridines having gastric acid secretion-inhibiting properties. The international Patent Applications WO98/42707 and WO98/54188 disclose tricyclic imidazopyridine derivatives having a very particular substitution pattern, which compounds are likewise said to be suitable for treating gastroin-testinal disorders.

DESCRIPTION OF THE INVENTION

The invention provides compounds of the formula 1

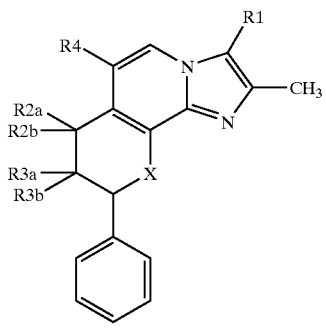

(1)

in which
R1 is methyl or hydroxymethyl,
one of the substituents R2a and R2b is hydrogen and the other is hydroxyl, methoxy, ethoxy, propoxy, isopropoxy, butoxy, methoxyethoxy or methoxypropoxy,
one of the substituents R3a and R3b is hydrogen and the other is hydrogen, hydroxyl, methoxy, ethoxy, propoxy, isopropoxy, butoxy, methoxyethoxy or methoxypropoxy,
R4 is halogen, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR5R6,
where
R5 is hydrogen, 1–7C-alkyl, hydroxy-1–4C-alkyl or 1–4C-alkoxy-1–4C-alkyl and
R6 is hydrogen, 1–7C-alkyl, hydroxy-1–4C-alkyl or 1–4C-alkoxy-1–4C-alkyl,
or where
R5 and R6 together with the nitrogen atom to which both are attached are a pyrrolidino, piperidino or morpholino radical,
X is O (oxygen) or NH,
and their salts,
except for those compounds in which R4 is chlorine or bromine if R2a or R2b is hydroxyl and simultaneously one of the substituents R3a and R3b is hydrogen and the other is hydrogen or hydroxyl.

For the purposes of the invention, halogen is bromine, chlorine or fluorine.

1–4C-Alkyl denotes straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1–4C-Alkoxy denotes radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

Hydroxy-1–4C-alkyl denotes the abovementioned 1–4C-alkyl radicals substituted by a hydroxyl group. Examples which may be mentioned are the hydroxymethyl, the 2-hydroxyethyl and the 3-hydroxypropyl radical.

1–4C-Alkoxy-1–4C-alkyl denotes one of the abovementioned 1–4C-alkyl radicals which is substituted by one of the abovementioned 1–4C-alkoxy radicals. Examples which may be mentioned are the methoxymethyl, the methoxyethyl and the butoxyethyl radical.

1–4C-Alkoxy-1–4C-alkoxy-1–4C-alkyl denotes one of the abovementioned 1–4C-alkoxy-4C-alkyl radicals which is substituted by one of the abovementioned 1–4C-alkoxy radicals. An example which may be mentioned is the methoxyethoxymethyl radical.

Fluoro-1–4C-alkoxy-1–4C-alkyl denotes one of the abovementioned 1–4C-alkyl radicals which is substituted by a fluoro-1–4C-alkoxy radical. Here, fluoro-1–4C-alkoxy denotes one of the 1–4C-alkoxy radicals which is fully or partly fluorine-substituted. Examples of fully or partly fluorine-substituted 1–4C-alkoxy which may be mentioned are the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy and the trifluoromethoxy and preferably the difluoromethoxy radical.

1–7C-Alkyl denotes straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

Suitable salts of compounds of the formula 1 are in particular all acid addition salts. Particular mention may be made of the pharmacologically acceptable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in the salt preparation in an equimolar ratio or a ratio differing therefrom, depending on whether the acid is a mono- or polybasic acid and on which salt is desired.

Pharmacologically unacceptable salts, which can be initially obtained, for example, as process products in the preparation of the compounds according to the invention on an industrial scale, are converted into the pharmacologically acceptable salts by processes known to the person skilled in the art.

It is known to the person skilled in the art that the compounds according to the invention and their salts can, for example when they are isolated in crystalline form, comprise varying amounts of solvents. The invention therefore also embraces all solvates and, in particular, all hydrates of the compounds of the formula 1, and all solvates and, in particular, all hydrates of the salts of the compounds of the formula 1.

The compounds of the formula 1 have at least two chiral centers. The invention provides all feasible stereoisomers in any mixing ratio, including the pure enantiomers which are the preferred subject matter of the invention.

One embodiment (embodiment a) of the invention are compounds of the formula 1, in which R4 is halogen.

A further embodiment (embodiment b) of the invention are compounds of the formula 1 in which R4 is carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR5R6.

Emphasis is given to compounds of the formula 1*

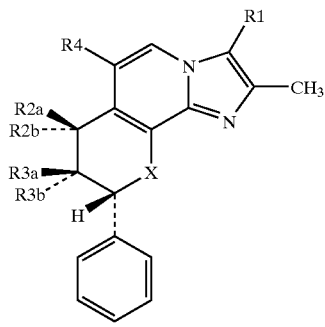

(1*)

in which
R1 is methyl or hydroxymethyl,
one of the substituents R2a and R2b is hydrogen and the other is hydroxyl, methoxy, ethoxy, propoxy, isopropoxy, butoxy, methoxyethoxy or methoxypropoxy,
one of the substituents R3a and R3b is hydrogen and the other is hydrogen, hydroxyl, methoxy, ethoxy, propoxy, isopropoxy, butoxy, methoxyethoxy or methoxypropoxy,
R4 is halogen, carboxyl, —CO-1–4C-alkoxy, hydroxy-1–4C-alkyl, 1–4C-alkoxy-1–4C-alkyl, 1–4 C-alkoxy-1–4C-alkoxy-1–4C-alkyl, fluoro-1–4C-alkoxy-1–4C-alkyl or the radical —CO—NR5R6,
where
R5 is hydrogen, 1–7C-alkyl, hydroxy-1–4C-alkyl or 1–4C-alkoxy-1–4C-alkyl and
R6 is hydrogen, 1–7C-alkyl, hydroxy-1–4C-alkyl or 1–4C-alkoxy-1–4C-alkyl,
or where
R5 and R6 together with the nitrogen atom to which both are attached are a pyrrolidino, piperidino or morpholino radical, X is O (oxygen) or NH, and its salts, except for those compounds in which R4 is chlorine or bromine if R2a is hydrogen and R2b is hydroxyl and simultaneously R3a is hydrogen or hydroxyl and R3b is hydrogen.

Compounds of embodiment a of the invention which are to be emphasized are those of the formula 1* in which R4 is halogen.

Compounds of embodiment b of the invention which are to be emphasized are those of the formula 1* in which R4 is carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR5R6.

Particular emphasis is to be given to compounds of the formula 1* in which

R1 is methyl,
one of the substituents R2a and R2b is hydrogen and the other is methoxy, ethoxy, propoxy, isopropoxy, butoxy, methoxyethoxy or methoxypropoxy,
one of the substituents R3a and R3b is hydrogen and the other is hydrogen or hydroxyl,
R4 is fluorine, chlorine, hydroxymethyl, methoxymethyl, methoxyethoxymethyl, difluoromethoxymethyl or the radical —CO—NR5R6, where R5 is hydrogen, methyl, ethyl, propyl, 2-hydroxyethyl or 2-methoxyethyl and R6 is hydrogen, methyl or ethyl, X is O (oxygen) or NH, and their salts.

Compounds of embodiment a of the invention which are to be particularly emphasized are those of the formula 1* in which R4 is fluorine or chlorine.

Compounds of embodiment b of the invention which are to be particularly emphasized are those of the formula 1* in which R4 is hydroxymethyl, methoxymethyl, methoxyethoxymethyl, difluoromethoxymethyl or the radical —CO—NR5R6, or 2-methoxyethyl and R6 is hydrogen, methyl or ethyl.

Among all the compounds of formula 1*, preference is given to those in which R3a is hydroxyl. In the Examples below, the absolute configuration "R" for both positions 8 and 9 has been assigned to these compounds of formula 1* in which R3a is hydroxyl.

The following exemplary preferred compounds according to the invention may be mentioned specifically using the general formula 1* and the meanings of the substituents R1, R2a, R2b, R3a, R3b, R4 and X of Table 1 (Tab. 1) below:

TABLE 1

| R1 | R2a | R2b | R3a | R3b | R4 | X |
|---|---|---|---|---|---|---|
| CH$_3$ | H | OCH$_3$ | OH | H | F | O |
| CH$_3$ | H | OC$_2$H$_5$ | OH | H | F | O |
| CH$_3$ | H | OCH(CH$_3$)$_2$ | OH | H | F | O |
| CH$_3$ | H | OCH$_2$CH$_2$OCH$_3$ | OH | H | F | O |
| CH$_3$ | H | OCH$_2$CH$_2$CH$_2$OCH$_3$ | OH | H | F | O |
| CH$_3$ | H | OCH$_3$ | OH | H | Cl | O |
| CH$_3$ | H | OC$_2$H$_5$ | OH | H | Cl | O |
| CH$_3$ | H | OCH(CH$_3$)$_2$ | OH | H | Cl | O |
| CH$_3$ | H | OCH$_2$CH$_2$OCH$_3$ | OH | H | Cl | O |
| CH$_3$ | H | OCH$_2$CH$_2$CH$_2$OCH$_3$ | OH | H | Cl | O |
| CH$_3$ | H | OCH$_3$ | H | H | F | O |
| CH$_3$ | H | OC$_2$H$_5$ | H | H | F | O |
| CH$_3$ | H | OCH(CH$_3$)$_2$ | H | H | F | O |
| CH$_3$ | H | OCH$_2$CH$_2$OCH$_3$ | H | H | F | O |
| CH$_3$ | H | OCH$_2$CH$_2$CH$_2$OCH$_3$ | H | H | F | O |
| CH$_3$ | H | OCH$_3$ | H | H | Cl | O |
| CH$_3$ | H | OC$_2$H$_5$ | H | H | Cl | O |
| CH$_3$ | H | OCH(CH$_3$)$_2$ | H | H | Cl | O |
| CH$_3$ | H | OCH$_2$CH$_2$OCH$_3$ | H | H | Cl | O |
| CH$_3$ | H | OCH$_2$CH$_2$CH$_2$OCH$_3$ | H | H | Cl | O |
| CH$_3$ | H | OCH$_3$ | OH | H | CO—N(CH$_3$)$_2$ | O |
| CH$_3$ | H | OC$_2$H$_5$ | OH | H | CO—N(CH$_3$)$_2$ | O |
| CH$_3$ | H | OCH(CH$_3$)$_2$ | OH | H | CO—N(CH$_3$)$_2$ | O |
| CH$_3$ | H | OCH$_2$CH$_2$OCH$_3$ | OH | H | CO—N(CH$_3$)$_2$ | O |
| CH$_3$ | H | OCH$_2$CH$_2$CH$_2$OCH$_3$ | OH | H | CO—N(CH$_3$)$_2$ | O |
| CH$_3$ | H | OCH$_3$ | H | H | CO—N(CH$_3$)$_2$ | O |
| CH$_3$ | H | OC$_2$H$_5$ | H | H | CO—N(CH$_3$)$_2$ | O |
| CH$_3$ | H | OCH(CH$_3$)$_2$ | H | H | CO—N(CH$_3$)$_2$ | O |
| CH$_3$ | H | OCH$_2$CH$_2$OCH$_3$ | H | H | CO—N(CH$_3$)$_2$ | O |
| CH$_3$ | H | OCH$_2$CH$_2$CH$_2$OCH$_3$ | H | H | CO—N(CH$_3$)$_2$ | O |
| CH$_3$ | H | OCH$_3$ | OH | H | CO—NH—CH$_2$CH$_2$—OH | O |
| CH$_3$ | H | OC$_2$H$_5$ | OH | H | CO—NH—CH$_2$CH$_2$—OH | O |
| CH$_3$ | H | OCH(CH$_3$)$_2$ | OH | H | CO—NH—CH$_2$CH$_2$—OH | O |
| CH$_3$ | H | OCH$_2$CH$_2$OCH$_3$ | OH | H | CO—NH—CH$_2$CH$_2$—OH | O |
| CH$_3$ | H | OCH$_2$CH$_2$CH$_2$OCH$_3$ | OH | H | CO—NH—CH$_2$CH$_2$—OH | O |
| CH$_3$ | H | OCH$_3$ | OH | H | CO—NH—CH$_2$CH$_2$—OCH$_3$ | O |
| CH$_3$ | H | OC$_2$H$_5$ | OH | H | CO—NH—CH$_2$CH$_2$—OCH$_3$ | O |
| CH$_3$ | H | OCH(CH$_3$)$_2$ | OH | H | CO—NH—CH$_2$CH$_2$—OCH$_3$ | O |
| CH$_3$ | H | OCH$_2$CH$_2$OCH$_3$ | OH | H | CO—NH—CH$_2$CH$_2$—OCH$_3$ | O |
| CH$_3$ | H | OCH$_2$CH$_2$CH$_2$OCH$_3$ | OH | H | CO—NH—CH$_2$CH$_2$—OCH$_3$ | O |
| CH$_3$ | H | OCH$_3$ | H | H | CO—NH—CH$_2$CH$_2$—OH | O |
| CH$_3$ | H | OC$_2$H$_5$ | H | H | CO—NH—CH$_2$CH$_2$—OH | O |
| CH$_3$ | H | OCH(CH$_3$)$_2$ | H | H | CO—NH—CH$_2$CH$_2$—OH | O |
| CH$_3$ | H | OCH$_2$CH$_2$OCH$_3$ | H | H | CO—NH—CH$_2$CH$_2$—OH | O |
| CH$_3$ | H | OCH$_2$CH$_2$CH$_2$OCH$_3$ | H | H | CO—NH—CH$_2$CH$_2$—OH | O |
| CH$_3$ | H | OCH$_3$ | H | H | CO—NH—CH$_2$CH$_2$—OCH$_3$ | O |
| CH$_3$ | H | OC$_2$H$_5$ | H | H | CO—NH—CH$_2$CH$_2$—OCH$_3$ | O |
| CH$_3$ | H | OCH(CH$_3$)$_2$ | H | H | CO—NH—CH$_2$CH$_2$—OCH$_3$ | O |
| CH$_3$ | H | OCH$_2$CH$_2$OCH$_3$ | H | H | CO—NH—CH$_2$CH$_2$—OCH$_3$ | O |
| CH$_3$ | H | OCH$_2$CH$_2$CH$_2$OCH$_3$ | H | H | CO—NH—CH$_2$CH$_2$—OCH$_3$ | O |
| CH$_3$ | H | OCH$_3$ | OH | H | CH$_2$OCH$_3$ | O |
| CH$_3$ | H | OC$_2$H$_5$ | OH | H | CH$_2$OCH$_3$ | O |
| CH$_3$ | H | OCH(CH$_3$)$_2$ | OH | H | CH$_2$OCH$_3$ | O |
| CH$_3$ | H | OCH$_2$CH$_2$OCH$_3$ | OH | H | CH$_2$OCH$_3$ | O |
| CH$_3$ | H | OCH$_2$CH$_2$CH$_2$OCH$_3$ | OH | H | CH$_2$OCH$_3$ | O |
| CH$_3$ | H | OCH$_3$ | H | H | CH$_2$OCH$_3$ | O |
| CH$_3$ | H | OC$_2$H$_5$ | H | H | CH$_2$OCH$_3$ | O |
| CH$_3$ | H | OCH(CH$_3$)$_2$ | H | H | CH$_2$OCH$_3$ | O |
| CH$_3$ | H | OCH$_2$CH$_2$OCH$_3$ | H | H | CH$_2$OCH$_3$ | O |
| CH$_3$ | H | OCH$_2$CH$_2$CH$_2$OCH$_3$ | H | H | CH$_2$OCH$_3$ | O |
| CH$_3$ | H | OCH$_3$ | H | H | CH$_2$OCHF$_2$ | O |
| CH$_3$ | H | OC$_2$H$_5$ | H | H | CH$_2$OCHF$_2$ | O |
| CH$_3$ | H | OCH(CH$_3$)$_2$ | H | H | CH$_2$OCHF$_2$ | O |
| CH$_3$ | H | OCH$_2$CH$_2$OCH$_3$ | H | H | CH$_2$OCHF$_2$ | O |
| CH$_3$ | H | OCH$_2$CH$_2$CH$_2$OCH$_3$ | H | H | CH$_2$OCHF$_2$ | O |
| CH$_3$ | H | OCH$_3$ | H | H | CH$_2$OCH$_2$CH$_2$OCH$_3$ | O |
| CH$_3$ | H | OC$_2$H$_5$ | H | H | CH$_2$OCH$_2$CH$_2$OCH$_3$ | O |
| CH$_3$ | H | OCH(CH$_3$)$_2$ | H | H | CH$_2$OCH$_2$CH$_2$OCH$_3$ | O |
| CH$_3$ | H | OCH$_2$CH$_2$OCH$_3$ | H | H | CH$_2$OCH$_2$CH$_2$OCH$_3$ | O |
| CH$_3$ | H | OCH$_2$CH$_2$CH$_2$OCH$_3$ | H | H | CH$_2$OCH$_2$CH$_2$OCH$_3$ | O |
| CH$_3$ | H | OCH$_3$ | OH | H | F | NH |
| CH$_3$ | H | OC$_2$H$_5$ | OH | H | F | NH |
| CH$_3$ | H | OCH(CH$_3$)$_2$ | OH | H | F | NH |
| CH$_3$ | H | OCH$_2$CH$_2$OCH$_3$ | OH | H | F | NH |
| CH$_3$ | H | OCH$_2$CH$_2$CH$_2$OCH$_3$ | OH | H | F | NH |
| CH$_3$ | H | OCH$_3$ | OH | H | Cl | NH |
| CH$_3$ | H | OC$_2$H$_5$ | OH | H | Cl | NH |

TABLE 1-continued

| R1 | R2a | R2b | R3a | R3b | R4 | X |
|---|---|---|---|---|---|---|
| CH$_3$ | H | OCH(CH$_3$)$_2$ | OH | H | Cl | NH |
| CH$_3$ | H | OCH$_2$CH$_2$OCH$_3$ | OH | H | Cl | NH |
| CH$_3$ | H | OCH$_2$CH$_2$CH$_2$OCH$_3$ | OH | H | Cl | NH |
| CH$_3$ | H | OCH$_3$ | H | H | F | NH |
| CH$_3$ | H | OC$_2$H$_5$ | H | H | F | NH |
| CH$_3$ | H | OCH(CH$_3$)$_2$ | H | H | F | NH |
| CH$_3$ | H | OCH$_2$CH$_2$OCH$_3$ | H | H | F | NH |
| CH$_3$ | H | OCH$_2$CH$_2$CH$_2$OCH$_3$ | H | H | F | NH |
| CH$_3$ | H | OCH$_3$ | H | H | Cl | NH |
| CH$_3$ | H | OC$_2$H$_5$ | H | H | Cl | NH |
| CH$_3$ | H | OCH(CH$_3$)$_2$ | H | H | Cl | NH |
| CH$_3$ | H | OCH$_2$CH$_2$OCH$_3$ | H | H | Cl | NH |
| CH$_3$ | H | OCH$_2$CH$_2$CH$_2$OCH$_3$ | H | H | Cl | NH |
| CH$_3$ | H | OCH$_3$ | OH | H | CO—N(CH$_3$)$_2$ | NH |
| CH$_3$ | H | OC$_2$H$_5$ | OH | H | CO—N(CH$_3$)$_2$ | NH |
| CH$_3$ | H | OCH(CH$_3$)$_2$ | OH | H | CO—N(CH$_3$)$_2$ | NH |
| CH$_3$ | H | OCH$_2$CH$_2$OCH$_3$ | OH | H | CO—N(CH$_3$)$_2$ | NH |
| CH$_3$ | H | OCH$_2$CH$_2$CH$_2$OCH$_3$ | OH | H | CO—N(CH$_3$)$_2$ | NH |
| CH$_3$ | H | OCH$_3$ | H | H | CO—N(CH$_3$)$_2$ | NH |
| CH$_3$ | H | OC$_2$H$_5$ | H | H | CO—N(CH$_3$)$_2$ | NH |
| CH$_3$ | H | OCH(CH$_3$)$_2$ | H | H | CO—N(CH$_3$)$_2$ | NH |
| CH$_3$ | H | OCH$_2$CH$_2$OCH$_3$ | H | H | CO—N(CH$_3$)$_2$ | NH |
| CH$_3$ | H | OCH$_2$CH$_2$CH$_2$OCH$_3$ | H | H | CO—N(CH$_3$)$_2$ | NH |
| CH$_3$ | H | OCH$_3$ | OH | H | CO—NH—CH$_2$CH$_2$—OH | NH |
| CH$_3$ | H | OC$_2$H$_5$ | OH | H | CO—NH—CH$_2$CH$_2$—OH | NH |
| CH$_3$ | H | OCH(CH$_3$)$_2$ | OH | H | CO—NH—CH$_2$CH$_2$—OH | NH |
| CH$_3$ | H | OCH$_2$CH$_2$OCH$_3$ | OH | H | CO—NH—CH$_2$CH$_2$—OH | NH |
| CH$_3$ | H | OCH$_2$CH$_2$CH$_2$OCH$_3$ | OH | H | CO—NH—CH$_2$CH$_2$—OH | NH |
| CH$_3$ | H | OCH$_3$ | OH | H | CO—NH—CH$_2$CH$_2$—OCH$_3$ | NH |
| CH$_3$ | H | OC$_2$H$_5$ | OH | H | CO—NH—CH$_2$CH$_2$—OCH$_3$ | NH |
| CH$_3$ | H | OCH(CH$_3$)$_2$ | OH | H | CO—NH—CH$_2$CH$_2$—OCH$_3$ | NH |
| CH$_3$ | H | OCH$_2$CH$_2$OCH$_3$ | OH | H | CO—NH—CH$_2$CH$_2$—OCH$_3$ | NH |
| CH$_3$ | H | OCH$_2$CH$_2$CH$_2$OCH$_3$ | OH | H | CO—NH—CH$_2$CH$_2$—OCH$_3$ | NH |
| CH$_3$ | H | OCH$_3$ | H | H | CO—NH—CH$_2$CH$_2$—OH | NH |
| CH$_3$ | H | OC$_2$H$_5$ | H | H | CO—NH—CH$_2$CH$_2$—OH | NH |
| CH$_3$ | H | OCH(CH$_3$)$_2$ | H | H | CO—NH—CH$_2$CH$_2$—OH | NH |
| CH$_3$ | H | OCH$_2$CH$_2$OCH$_3$ | H | H | CO—NH—CH$_2$CH$_2$—OH | NH |
| CH$_3$ | H | OCH$_2$CH$_2$CH$_2$OCH$_3$ | H | H | CO—NH—CH$_2$CH$_2$—OH | NH |
| CH$_3$ | H | OCH$_3$ | H | H | CO—NH—CH$_2$CH$_2$—OCH$_3$ | NH |
| CH$_3$ | H | OC$_2$H$_5$ | H | H | CO—NH—CH$_2$CH$_2$—OCH$_3$ | NH |
| CH$_3$ | H | OCH(CH$_3$)$_2$ | H | H | CO—NH—CH$_2$CH$_2$—OCH$_3$ | NH |
| CH$_3$ | H | OCH$_2$CH$_2$OCH$_3$ | H | H | CO—NH—CH$_2$CH$_2$—OCH$_3$ | NH |
| CH$_3$ | H | OCH$_2$CH$_2$CH$_2$OCH$_3$ | H | H | CO—NH—CH$_2$CH$_2$—OCH$_3$ | NH |
| CH$_3$ | H | OCH$_3$ | OH | H | CH$_2$OCH$_3$ | NH |
| CH$_3$ | H | OC$_2$H$_5$ | OH | H | CH$_2$OCH$_3$ | NH |
| CH$_3$ | H | OCH(CH$_3$)$_2$ | OH | H | CH$_2$OCH$_3$ | NH |
| CH$_3$ | H | OCH$_2$CH$_2$OCH$_3$ | OH | H | CH$_2$OCH$_3$ | NH |
| CH$_3$ | H | OCH$_2$CH$_2$CH$_2$OCH$_3$ | OH | H | CH$_2$OCH$_3$ | NH |
| CH$_3$ | H | OCH$_3$ | H | H | CH$_2$OCH$_3$ | NH |
| CH$_3$ | H | OC$_2$H$_5$ | H | H | CH$_2$OCH$_3$ | NH |
| CH$_3$ | H | OCH(CH$_3$)$_2$ | H | H | CH$_2$OCH$_3$ | NH |
| CH$_3$ | H | OCH$_2$CH$_2$OCH$_3$ | H | H | CH$_2$OCH$_3$ | NH |
| CH$_3$ | H | OCH$_2$CH$_2$CH$_2$OCH$_3$ | H | H | CH$_2$OCH$_3$ | NH |
| CH$_3$ | H | OCH$_3$ | H | H | CH$_2$OCHF$_2$ | NH |
| CH$_3$ | H | OC$_2$H$_5$ | H | H | CH$_2$OCHF$_2$ | NH |
| CH$_3$ | H | OCH(CH$_3$)$_2$ | H | H | CH$_2$OCHF$_2$ | NH |
| CH$_3$ | H | OCH$_2$CH$_2$OCH$_3$ | H | H | CH$_2$OCHF$_2$ | NH |
| CH$_3$ | H | OCH$_2$CH$_2$CH$_2$OCH$_3$ | H | H | CH$_2$OCHF$_2$ | NH |
| CH$_3$ | H | OCH$_3$ | H | H | CH$_2$OCH$_2$CH$_2$OCH$_3$ | NH |
| CH$_3$ | H | OC$_2$H$_5$ | H | H | CH$_2$OCH$_2$CH$_2$OCH$_3$ | NH |
| CH$_3$ | H | OCH(CH$_3$)$_2$ | H | H | CH$_2$OCH$_2$CH$_2$OCH$_3$ | NH |
| CH$_3$ | H | OCH$_2$CH$_2$OCH$_3$ | H | H | CH$_2$OCH$_2$CH$_2$OCH$_3$ | NH |
| CH$_3$ | H | OCH$_2$CH$_2$CH$_2$OCH$_3$ | H | H | CH$_2$OCH$_2$CH$_2$OCH$_3$ | NH | and the salts of these compounds.

The compounds according to the invention can be prepared as described in the examples below in an exemplary manner, or by employing similar process steps using appropriate starting materials (see, for example, WO 98/42707, WO 98/54188, EP-A-299470 or Kaminski et al., J. Med. Chem. 1985, 28, 876–892 and Angew. Chem. 1996, 108, 589–591). The starting materials are known, or they can be prepared in a manner similar to that for known compounds. The compounds according to the invention can be prepared, for example, in accordance with the reaction schemes below.

Scheme 1

In the scheme below, the preparation of compounds of the formula 1 according to the invention where R1 = CH$_3$, R2a or R2b and R3a or R3b = hydroxyl and X = O (oxygen) is outlined in an exemplary manner:

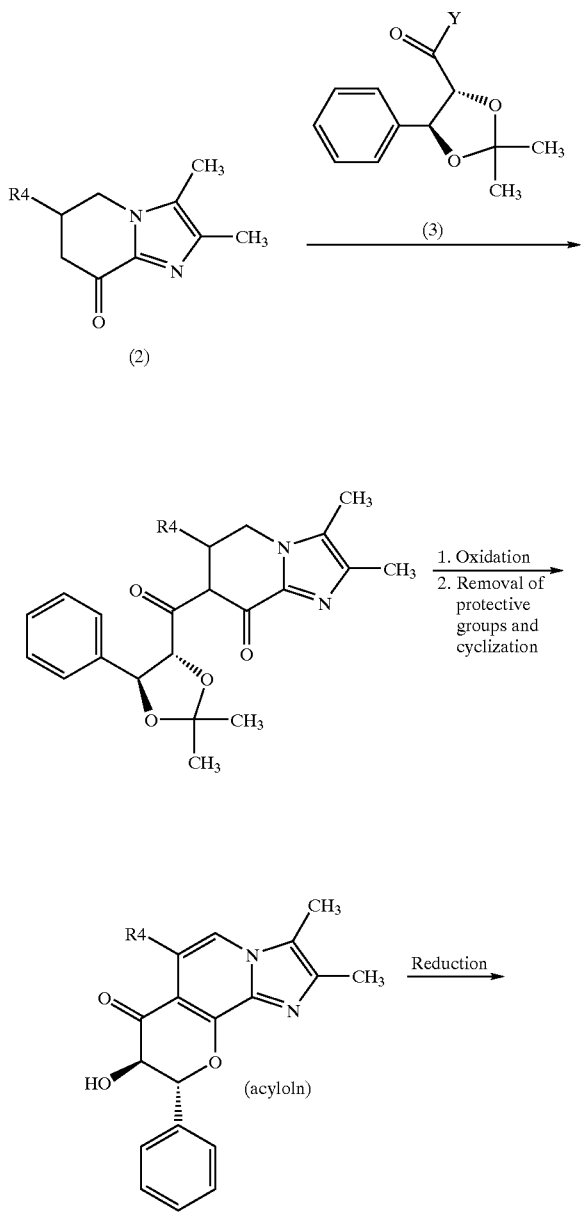

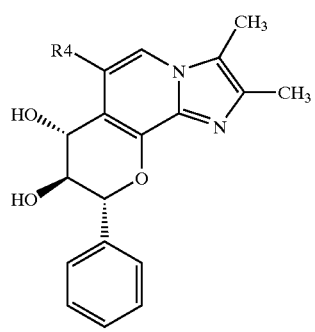

In scheme 1 above, the enantioselective synthesis of a 7,8-diol according to the invention (R2a or R2b and R3a or R3b are in each case hydroxyl) is shown in an exemplary manner; if desired, the diol can subsequently be etherified in a suitable manner.

Group Y in compound 3 above is a suitable leaving group, for example a halogen atom, preferably chlorine. The acylation is carried out in a manner familiar to the person skilled in the art, preferably using sodium bis(trimethylsilyl)amide or potassium bis(trimethylsilyl)amide, if the leaving group is a chlorine atom.

The oxidation that follows after the acylation is likewise carried out under customary conditions using the oxidizing agent chloranil, atmospheric oxygen or manganese dioxide. For the subsequent removal of protective groups and cyclization, certain conditions have to be met with respect to the auxiliary acid used. Advantageously, the auxiliary acid used according to the invention is formic acid.

The reduction to the diol is likewise carried out under standard conditions (see, for example, WO 98/54188), where the reducing agent used is, for example, sodium borohydride, the use of which allows the given 7,8-trans-diol to be obtained in a diastereomeric purity of more than 90%. Etherification, which is carried out subsequently, if desired, and which is likewise carried out in a usual manner, gives the compounds of the formula 1* according to the invention in which R2a and R3b are hydrogen.

To prepare compounds of the formula 1 in which R3a and R3b are hydrogen, 3-hydroxy-3-phenylpropionic acid derivatives (which are appropriately protected at the hydroxyl group), in which Y (analogously to the scheme above) is a suitable leaving group, have to be used as starting materials in place of compound 3.

Scheme 2

In the scheme below, the preparation of compounds of the formula 1 according to the invention where R1 = CH₃, R2a or R2b = hydroxyl and X = NH is outlined in an exemplary manner using compounds of the formula 2 (see scheme 1) as starting materials:

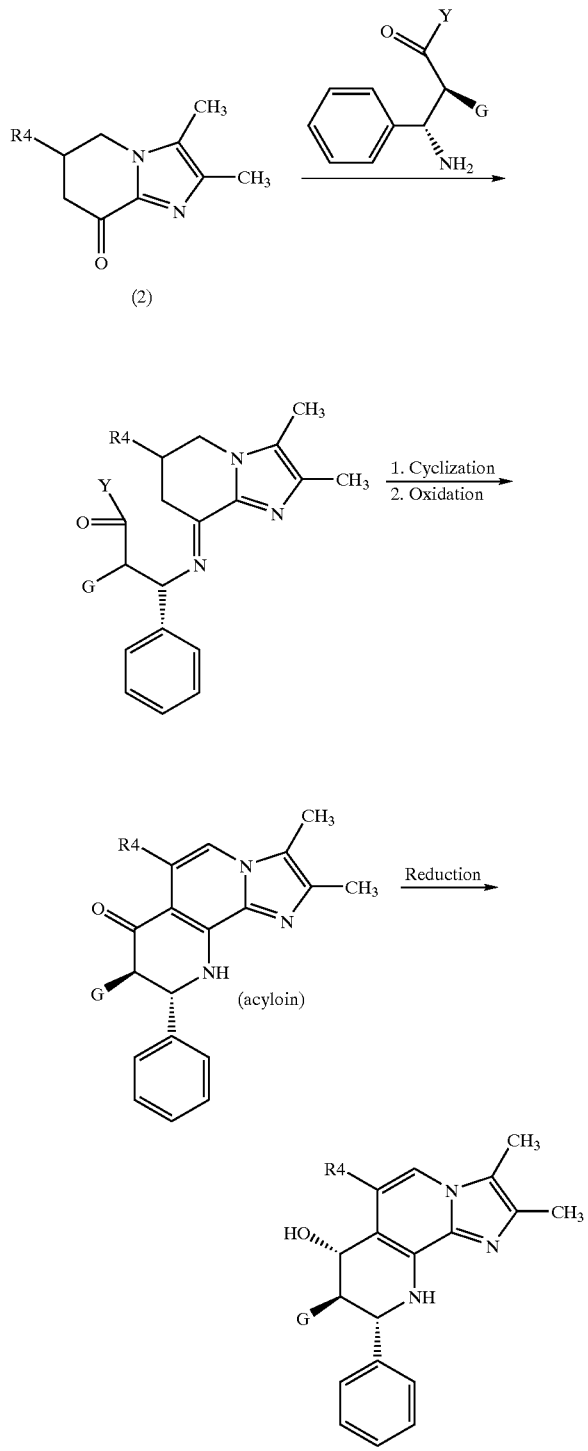

Scheme 2 above also represents, in an exemplary manner, an enantioselective synthesis. Y again denotes a suitable leaving group, for example a methoxy group. Depending on whether a compound where R3a and R3b=hydrogen or a compound where R3a or R3b=hydroxyl is desired, the group G denotes either hydrogen or a hydroxyl group (which is, for example, protected by a suitable silyl radical).

Reduction of the keto group with sodium borohydride, which follows after the cyclization, gives—if G is a hydroxyl group—the 7,8-trans-diol in a diastereomeric purity of more than 90%. Subsequent etherification, which is carried out by known processes, gives the end products of the formula 1* in which R2a and R3b are hydrogen. The corresponding 7,8-cis compound is obtained by chromatographic purification from the mother liquor which remains after the 7,8-trans compound has been separated off.

The substances according to the invention are isolated and purified in a manner known per se, for example by distilling off the solvent under reduced pressure and recrystallizing the resulting residue from a suitable solvent, or by subjecting it to one of the customary purification methods, such as, for example, column chromatography on a suitable stationary phase.

Salts are obtained by dissolving the free compound in a suitable solvent, for example in a chlorinated hydrocarbon, such as methylene chloride or chloroform, or in a low-molecular-weight aliphatic alcohol (ethanol, isopropanol) which contains the desired acid or to which the desired acid is subsequently added. The salts are obtained by filtration, reprecipitation, precipitation with a nonsolvent for the addition salt or by evaporating the solvent. The resulting salts can be converted by alkalization or acidification into the free compounds which in turn can be used to prepare salts. In this manner, it is possible to convert pharmacologically unacceptable salts into pharmacologically acceptable salts.

The pure enantiomers, in particular the pure enantiomers of the formula 1*, which are preferably provided by the invention, can be obtained in a manner familiar to the person skilled in the art, for example by enantioselective synthesis (see, for example, the scheme), by chromatographic separation on chiral separation columns, by derivatization with chiral auxiliaries, subsequent separation of the diastereomers and removal of the chiral auxiliary group, by salt formation with chiral acids, subsequent separation of the salts and liberation of the desired compound from the salt, or by (fractional) crystallization from a suitable solvent.

The resulting etherified trans products (for example compounds 1* where R2a and R3b=hydrogen) can—at least partially—be converted into the corresponding cis products (for example where R2b and R3b=hydrogen) by allowing the product to stand under acidic conditions (for example in 2 equivalents of acid, such as sulfuric acid) in the corresponding alcohol R2a—OH. Likewise, cis products can be converted into the corresponding trans products. The cis and trans products are separated, for example, by chromatography or by crystallization.

The starting materials of the formula 2 can be prepared from compounds known from the literature or by working analogously to processes known from the literature (for example Kaminski et al., J. Med. Chem. 1985, 28, 876–892), for example according to the general scheme 3 below:

Scheme 3

In the scheme below, the preparation of the starting compounds 2 where
R4 = ——COOC₂H₅ or R4 = ——CH₂OCH₃ is outlined in an examplary manner.

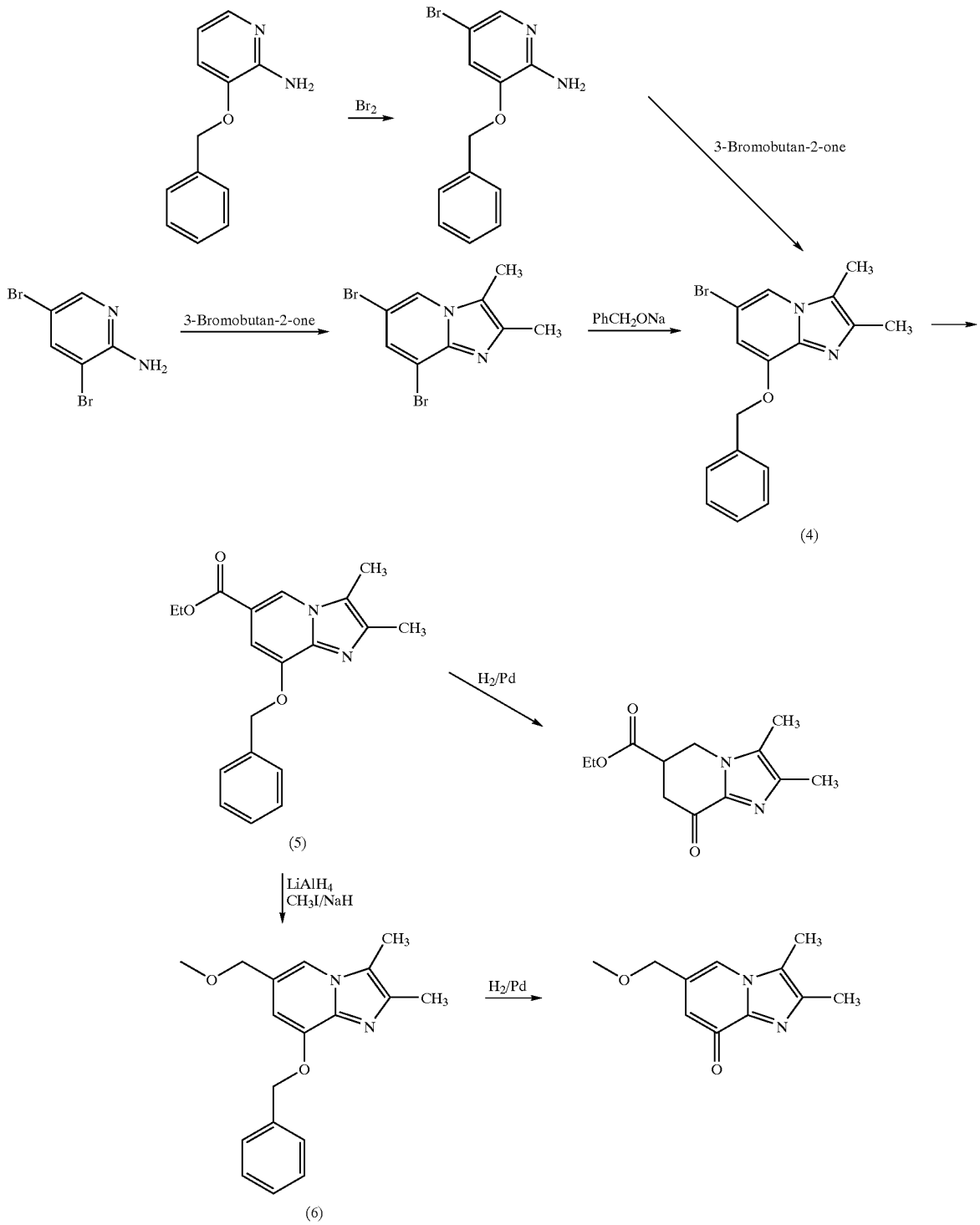

The conversion into compound 4 is carried out in a manner known to the person skilled in the art. Conversion of 4 into 5 can be carried out by different routes, for example using the Heck reaction (with Pd(II), carbon monoxide and ethanol) or by metallation in the 6-position (with lithium or magnesium) and subsequent Grignard reaction. By metallation, it is also possible to introduce other desired groups R4 into position 6, for example fluorine, chlorine or the carboxyl group. Starting with the ester group, it is possible to introduce further desired groups R4 into position 6, for example hydroxy-1–4C-alkyl radicals (in particular the hydroxymethyl radical) by reducing the ester radical with lithium aluminum hydride, or 1–4C-alkoxy-1–4C-alkyl radicals (in particular 1–4C-alkoxymethyl radicals) by subsequent etherification as outlined in Scheme 3.

Debenzylation/reduction of the compounds 5 and 6 is likewise carried out in a manner known per se, for example by using hydrogen/Pd(O). If the desired compounds are compounds where R4=—CO—NR5R6, a corresponding derivatization can be carried out in a manner known per se (conversion of an ester into an amide) at the stage of compound 5 or after debenzylation/reduction, or alternatively at the stage of the acyloin (see Schemes 1 and 2).

The following examples illustrate the invention in more detail, without limiting it. Further compounds of the formula 1 whose preparation is not described explicitly can likewise be prepared in an analogous manner or in a manner known per se to the person skilled in the art, using customary process techniques. The abbreviation min stands for minute (s), h stands for hour(s) and ee stands for enantiomeric excess. In some successive examples the preparation of pairs of diastereoisomers is described. In case of the pairs 7R,8R, 9R/7S,8R,9R, the diastereoisomers can be separated by column chromatography with the 7S,8R,9R diastereolsomer being contained in the first and the 7R,8R,9R diastereoisomer being contained in the second main fraction.

EXAMPLES 1. 6,8-Dibromo-2,3-dimethylimidazo[1,2-a]pyridine

A mixture of 31.8 g of 2-amino-3,5-dibromopyridine, 22 g of 3-bromo-2-butanone and 350 ml of tetrahydrofuran is heated under reflux for 9 days, and the precipitate formed is filtered off and dried in vacuo. It is then suspended in 1 l of water and the suspension is adjusted to pH 8 using 6 molar aqueous sodium hydroxide solution. The precipitate formed here is filtered off and washed with water. 28 g of the title compound of melting point over 90° C. (sintering) are obtained.

2. 8-Benzyloxy-6-bromo-2,3-dimethylimidazd[1,2-a]pyridine 34.8 ml of benzyl alcohol are added dropwise with ice-cooling to a suspension of 13.5 g of sodium hydride (60% strength suspension in paraffin) in 510 ml of dimethylformamide and the mixture is stirred for 1 h until the generation of gas is complete. 51.2 g of 6,8-dibromo-2,3-dimethylimidazo[1,2-a]pyridine are then introduced in small portions and the mixture is stirred at room temperature for 40 h. It is then poured onto 1 l of ice water, extracted three times with 100 ml of dichloromethane each time, the combined organic extracts are washed with saturated aqueous ammonium chloride solution and twice with water and concentrated to dryness in vacuo, and the residue is stirred with a little ethyl acetate. The precipitate obtained here is filtered off and dried in vacuo. 43.2 g of the title compound of melting point 151–3° C. (ethyl acetate) are obtained.

3. 8-Benzyloxy-6-ethoxycarbonyl-2,3-dimethylimidazo[1, 2-a]pyrldine

A mixture of 4 g of 8-benzyloxy-6-bromo-2,3-dimethylimidazo[1,2-a]pyridine, 0.4 g of palladium(II) acetate, 1.33 g of triphenylphosphine, 10 ml of triethylamine and 50 ml of ethanol is heated for 16 h in a carbon monoxide atmosphere in an autoclave (5 bar), the volatile portions are stripped off in vacuo and the residue is chromatographed on silica gel (eluent: ethyl acetate). 2.4 g of the title compound of melting point 140–1° C. (diethyl ether) are obtained. 4. 6-Ethoxycarbonyl-2,3-dimethyl-5,6,7,8-tetrahydrolmidazo[1,2-a]pyridine-8-one 3 g of 8-benzyloxy-6-ethoxycarbonyl-2,3-dimethylimidazo[1,2-a]pyridine, suspended in 50 ml of ethanol, are treated with 0.5 g of 10% strength palladium/active carbon and hydrogenated under a hydrogen pressure of 50 bar for 20 hours at an oil bath temperature of 75° C. After cooling, the catalyst is filtered off, the filtrate is concentrated to ⅕ of the volume in vacuo and the colorless precipitate formed here is filtered off. The filtrate from the precipitate is concentrated to dryness and chromatographed on silica gel (eluent: methylene chloride/methanol 100/3). 0.32 g of 6-ethoxycarbonyl-8-hydroxy-2,3-dimethyl-5,6,7, 8-tetrahydroimidazo[1,2-a]pyridine is obtained. For conversion into the title compound, it is dissolved in chloroform, treated with 1.6 g of manganese dioxide and stirred at room temperature for 20 h. It is then filtered off, the filtrate is concentrated to dryness in vacuo and the residue obtained is purified on silica gel (eluent: methylene chloride/methanol 13/1). 0.2 g of the title compound of melting point 138–40° C. (diethyl ether) is obtained.

5. 8-Benzyloxy-6-hydroxymethyl-2,3-dimethylimidazo[1,2-a]pyridine

A solution of 1.2 g of 8-benzyloxy-6-ethoxycarbonyl-2, 3-dimethylimidazo[1,2-a]pyridine in 20 ml of tetrahydrofuran is treated in small portions with 0.2 g of lithium aluminum hydride at room temperature, stirred for one hour and treated successively with 0.2 ml of water, 0.2 ml of 6 molar sodium hydroxide solution and 0.6 ml of water. It is then extracted twice with methylene chloride (50 ml each), the combined organic phases are concentrated to dryness in vacuo and the residue is purified on silica gel (eluent: methylene chloride/methanol 13/1). 0.4 g of the title compound of melting point 213–5° C. (acetone) is obtained.

6. 6-Hydroxymethyl-2,3-dimethyl-5,6,7,8-tetrahydrolmidazo[1,2-a]pyridin-8-one

Analogously to the process described in Example 4, the title compound is obtained starting from 8-benzyloxy-6-hydroxymethyl-2,3-dimethylimidazo[1,2-a]pyridine by debenzylation/hydrogenation with palladium/active carbon.

7. 2,3-Dimethyl-6,7-dihydro-5H-imidazo[1,2-a]pyridin-8-one a) 500 g (2.35 mol) of 8-amino-2,3-dimethylimidazo[1, 2-a]pyridine (see EP-A-299470) and 150 g of palladium on active carbon (10% Pd), suspended in 5.0 l of 6N hydrochloric acid, are stirred at 50° C. for 24 h under a hydrogen pressure of 10 bar. The catalyst is filtered off and the reaction mixture is concentrated to 2.0 l in vacuo. The solution obtained is extracted with dichloromethane. The aqueous phase is adjusted to pH 4.8–5.0 using concentrated ammonia solution and again extracted with dichloromethane. This procedure is repeated ten times. The combined organic phases are dried over sodium sulfate and concentrated. The crude product is crystallized from isopropanol. 334.1 g of the title compound are obtained in the form of pale brown crystals of melting point 178.5° C. (isopropanol).

Alternatively, the title compound can be prepared as follows:

b) A mixture of 252 g of 8-benzyloxy-2,3-dimethylimdazo[1,2-a]pyridine, 84 g of sodium hydrogencarbonate and 27 g of palladium/carbon catalyst (10% strength) in 500 ml of methanol is initially hydrogenated at 40° C. with hydrogen (5 bar) in an autoclave (20 h). The temperature is then reduced to 20° and the hydrogen pressure to 2 bar and hydrogenation is continued until the slow absorption of hydrogen is complete (about 10 h, TLC checking). The catalyst is then filtered off, the filter cake is washed with 200 ml of methanol, the filtrate is concentrated to dryness in vacuo, the residue is stirred with 200 ml of chloroform and insoluble material is filtered off. The filter cake is washed thoroughly with 150 ml of chloroform and the filtrate is concentrated to dryness in vacuo. 142 9 of the title compound of melting point 178–9° C. (2-propanol) are obtained.

8. 3-Formyl-2-methyl-6,7-dihydro-5H-imidazo[1,2-a]pyridin-8-one

Analogously to the process described in Example 7a, the title compound is obtained starting from the compound 8-amino-3-formyl-2-methylimidazo[1,2-a]pyridine described in EP-A-299470.

9. 6-Chloro-3-formyl-2-methyl-6,7-dihydro-5H-imidazo[1,2-a]pyridin-8-one

Analogously to the process described in Example 4, the title compound is obtained starting from 8-benzyloxy-6-chloro-3-formyl-2-methylimidazo[1,2-a]pyridine (EP-A-299470) by debenzylation/hydrogenation with palladium/active carbon.

10. 8-Benzyloxy-6-methoxymethyl-2,3-dimethylimidazo[1,2-a]pyridine

Under an atmosphere of inert gas, a suspension of 1.2 g of 8-benzyloxy-6-hydroxymethyl-2,3-dimethylimidazo[1,2-a]pyridine in 12 ml of dimethylformamide is admixed with 0.36 g of 60% sodium hydride in paraffin, and the mixture is stirred at room temperature for 30 minutes, until the generation of gas has ceased, and then, at room temperature, admixed with 0.56 ml of methyl iodide. After a reaction time of one hour, the mixture is poured into 100 ml of ice-water and extracted three times with in each case 100 ml of ethyl acetate. The organic phases are combined and washed with water. The solvent is removed in vacuo and the oily residue is chromatographed on silica gel (mobile phase: methylene chloridelmethanol=100/1). This gives 0.34 g of the title compound of melting point 107° C. (diethyl ether).

11. 6-Methoxymethyl-2,3-dimethyl-5,6,7,8-tetrahydrolmidazo[1,2-a]pyridin-8-one 19.2 g of 8-benzyloxy-6-methoxymethyl-2,3-dimethylimidazo[1,2-a]pyridine, dissolved in 100 ml of methanol, are admixed with 1.9 g of palladium (10% on carbon, from Merck) and hydrogenated with hydrogen at 80° C., using a pressure of 50 bar. After the uptake of hydrogen has ended, the catalyst is filtered off and washed with methanol and methylene chloride, and the combined filtrates are concentrated to dryness in vacuo. Purification on silica gel (mobile phase: methylene chloride/ methanol=13/1) gives 7.6 g of the title compound of melting point 103–104° C.

12. (8R, 9R)-8-(t-Butydimethylsilyloxy)-6-methoxymethyl-2,3-dimethyl-9-phenyl-5,6,7,8,9,10-hexahydroimidazo[1,2-h][1,7]naphthyridin-7-one By using a water separator, a mixture of 2.66 g of 6-methoxymethyl-2,3-dimethyl-5,6,7,8-tetrahydroimidazo[1,2-a]pyridin-8-one, 4.27 g of ethyl (2R, 3R)-3-amino-2-(t-butyldimethylsilyloxy)-3-phenylpropionate, 70 mg of p-toluenesulfonic acid and 15 ml of toluene is boiled at reflux for 1.5 h. After cooling, 15 ml of tetrahydrofuran are added. With introduction of argon, the mixture is cooled to an internal temperature of −25° C. 15.4 ml of a commercial 2 molar solution of lithium diisopropylamide (Aldrich) are then added. The solution is stirred at −25° C. for 30 min. The solution is then allowed to warm to room temperature (30 min.) and poured into 30 ml of saturated aqueous ammonium chloride solution, the mixture is extracted three times with in each case 20 ml of ethyl acetate and the combined extracts are concentrated to dryness in vacuo. Purification on silica gel (mobile phase: methylene chloride/methanol=100/3) gives 5.2 g of the title compound as a yellowish amorphous solid. $^1$H-NMR(CDCl$_3$, δ), 7.33–7.45 (m, 5H), 5.95 (d, 1H), 4.55–4.65 (dd, 1H), 4.2–4.4 (dd, 2H), 3.2–3.75 (m, 3H), 3.3 (s, 3H), 2.91–3.1 (q, 1H), 2.15 (s, 6H), 0.6 (d, 9H), 0.08 (d, 3H), −0.3 (d, 3H).

13. (8R, 9R)-8-(t-Butyldimethylsilyloxy)-6-methoxymethyl-2,3-dimethyl-9-phenyl-7,8,9,10-tetrahydrolmidazo[1,2-h][1,7]naphthyridin-7-one A mixture of 8.35 g of (8R, 9R)-8-(t-butyldimethylsilyloxy)-6-methoxymethyl-2,3-dimethyl-9-phenyl-5,6,7,8,9,10-hexahydroimidazo[1,2-h][1,7]naphthyridin-7-one and 50 g of manganese dioxide in 160 ml of chloroform is heated at reflux for 16 hours, admixed with another 40 g of manganese dioxide and boiled at reflux for another 24 hours. After cooling, solid components are filtered off and washed with methylene chloride, and the combined filtrates are concentrated to dryness in vacuo. Purification on silica gel (mobile phase: methylene chloride/methanol=100/1) gives 0.85 9 of the title compound as an amorphous solid. $^1$H-NMR(CDCl$_3$, δ), 7.2–7.5 (m, 7H), 4.3–4.7 (m, 4H), 3.4 (s, 3H), 2.35 (s, 3H), 2.3 (s, 3H), 0.65 (s, 9H), 0.02 (s, 3H), −0.2 (s, 3H).

14. (8R, 9R)-8-Hydroxy-6-methoxymethyl-2,3-dimethyl-9-phenyl-7,8,9,10-tetrahydrolmidazo-[1,2-h][1,7]naphthyridin-7-one A solution of 0.8 g of (8R, 9R)-8-(t-butyldimethylsilyloxy)-6-methoxymethyl-2,3-dimethyl-9-phenyl-7,8,9,10-tetrahydroimidazo[1,2-h][1,7]naphthyridin-7-one in 8 ml of tetrahydrofuran is admixed with 2 ml of a commercial solution of tetrabutylammonium fluoride in THF (1M solution), stirred at room temperature for 3 hours and then admixed with 50 ml of sodium hydrogen carbonate solution (saturated in water) and extracted 3 times with in each case 50 ml of ethyl acetate, the combined organic phases are concentrated to dryness in vacuo and the solid that remains is purified on silica gel (mobile phase: ethyl acetate/petroleum ether=1:1). This gives 0.41 g of the title compound of melting point 206–208° C.

15. (7S,8R,9R)-7,8-Dihydroxy-6-methoxymethyl-2,3-dimethyl-9-phenyl-7,8,9,10-tetrahydroimidazo[1,2-h][1,7]naphthyridine At room temperature, 0.2 g of sodium borohydride are added in small portions to 0.4 g of (8R, 9R)-8-hydroxy-6-methoxymethyl-2,3-dimethyl-9-phenyl-7,8,9,10-tetrahydroimidazo[1,2-h][1,7]naphthyridin-7-one, dissolved in 20 ml of methanol, and the mixture is stirred at room temperature for 2 hours. The solvent is then removed under reduced pressure and the residue is admixed with water and extracted 3 times with methylene chloride. The organic phases are combined and concentrated to dryness in vacuo. Purification on silica gel (mobile phase: methylene chloride/methanol=100/3) gives 80 mg of the title compound [R$_f$=0.54 (methylene chloride/methanol=13/1)] of melting point 182–3° C. (decomp.).

16. (7R,8R,9R)-7,8-Dihydroxy-6-methoxymethyl-2,3-dimethyl-9-phenyl-7,8,9,10-tetrahydroimidazo[1,2-h][1,7]naphthyridine 0.4 g of (8R, 9R)-8-hydroxy-6-methoxymethyl-2,3-dimethyl-9-phenyl-7,8,9,10-tetrahydroimidazo[1,2-h]-[1,7]naphthyridin-7-one are reacted with sodium borohydride analogously to Example 15. After purification on silica gel (mobile phase: methylene chloride/methanol=100/3), 120 mg of the title compound [R$_f$=0.44 (methylene chloride/methanol=13/1)] of melting point 202–5° C. (decomp.) are obtained.

17. (7S,8R,9R)-8-Hydroxy-7-methoxy-6-methoxymethyl-2,3-dimethyl-9-phenyl-7,8,9,10-tetrahydroimidazo[1,2-h][1,7]naphthyridine 180 mg of (7R,8R,9R)-7,8-dihydroxy-6-methoxymethyl-2,3-dimethyl-9-phenyl-7,8,9,10-tetrahydro-imidazo[1,2-h][1,7]naphthyridine, dissolved in 10 ml of methanol, are admixed with 110 mg of concentrated sulfuric acid and allowed to stand at room temperature for 16 hours. The mixture is then diluted with 100 ml of water and adjusted to pH 8 using aqueous 1N sodium hydroxide solution and aqueous saturated sodium hydrogen carbonate solution and extracted 3 times with in each case 50 ml of methylene chloride. The combined organic phases are evaporated to dryness in vacuo and the residue is chromatographed on silica gel (mobile phase: methylene chloride/methanol=100/3). This gives 100 mg of the title compound [$R_f$=0.62 (methylene chloride/methanol=13/1)] of melting point 126–9° C. (decomp.).

18. (7R,8R,9R)-8-Hydroxy-7-methoxy-6-methoxymethyl-2,3-dimethyl-9-phenyl-7,8,9,10-tetrahydrohydroimidazo[1,2-h][1,7]naphthyridine Reaction of (7R,8R,9R)-7,8-dihydroxy-6-methoxymethyl-2,3-dimethyl-9-phenyl-7,8,9,10-tetrahydroimidazo[1,2-h][1,7]naphthyridine with sulfuric acid and methanol analogously to Example 17 and purification on silica gel (mobile phase: methylene chloride/methanol=100/3) gives 30 mg of the title compound [$R_f$=0.52 (methylene chloride/methanol=13/1)] of melting point 181–3° C. (decomp.).

19. (7R,8R,9R)-8-Hydroxy-7-(2-methoxyethoxy)-6-methoxymethyl-2,3-dimethyl-9-phenyl-7,8,9,10-tetrahydroimidazo[1,2-h][1,7]naphthyridine Analogously to Example 15, 250 mg of the title compound [$R_f$=0.45 (methylene chloride/methanol=13/1)] of melting point 158–60° C. are obtained by reacting (7R,8R,9R)-7,8-dihydroxy-6-methoxymethyl-2,3-dimethyl-9-phenyl-7,8,9,10-tetrahydroimidazo[1,2-h][1,7]naphthyridine with 2-methoxyethanol and purification on silica gel (mobile phase: methylene chloride/methanol=100/3).

20. (7S,8R,9R)-8-Hydroxy-7-(2-methoxyethoxy)-6-methoxymethyl-2,3-dimethyl-9-phenyl-7,8,9,10-tetrahydroimidazo[1,2-h][1,7]naphthyridine Analogously to Example 15, 440 mg of the title compound [$R_f$=0.60 (methylene chloride/methanol=13/1)] of melting point 158–60° C. (decomp.) are obtained by reacting 700 mg of (7R,8R,9R)-7,8-dihydroxy-6-methoxymethyl-2,3-dimethyl-9-phenyl-7,8,9,10-tetrahydroimidazo-[1,2-h][1,7]naphthyridine with 2-methoxyethanol and purification on silica gel (mobile phase: methylene chloride/methanol=100/3).

21. (7R,8R,9R)-8-Hydroxy-7-ethoxy-6-methoxymethyl-2,3-dimethyl-9-phenyl-7,8,9,10-tetrahydroimidazo[1,2-h][1,7]naphthyridine Analogously to Example 15, 350 mg of the title compound [$R_f$=0.45 (methylene chloride/methanol=13/1)] of melting point 184–6° C. (decomp.) are obtained by reaction of (7R,8R,9R)-7,8-dihydroxy-6-methoxymethyl-2,3-dimethyl-9-phenyl-7,8,9,10-tetrahydroimidazo[1,2-h][1,7]naphthyridine with ethanol and purification on silica gel (mobile phase: methylene chloride/methanol=100/3).

22. (7S,8R,9R)-8-Hydroxy-7-ethoxy-6-methoxymethyl-2,3-dimethyl-9-phenyl-7,8,9,10-tetrahydroimidazo[1,2-h][1,7]naphthyridine Analogously to Example 15, 230 mg of the title compound [$R_f$=0.60 (methylene chloride/methanol=13/1)] of melting point 163–4° C. (decomp.) are obtained by reaction of 700 mg of (7R,8R,9R)-7,8-dihydroxy-6-methoxymethyl-2,3-dimethyl-9-phenyl-7,8,9,10-tetrahydroimidazo[1,2-h][1,7]naphthyridine with ethanol and purification on silica gel (mobile phase: methylene chloride/methanol=100/3).

Commercial Utility

The compounds of the formula I and their salts have valuable pharmacological properties which make them commercially utilizable. In particular, they exhibit marked inhibition of gastric acid secretion and an excellent gastric and intestinal protective action in warm-blooded animals, in particular humans. In this connection, the compounds according to the invention are distinguished by a high selectivity of action, an advantageous duration of action, a particularly good enteral activity, the absence of significant side effects and a large therapeutic range.

"Gastric and intestinal protection" in this connection is understood as meaning the prevention and treatment of gastrointestinal diseases, in particular of gastrointestinal inflammatory diseases and lesions, and of gastric acid-related diseases in mammals including man (such as, for example, gastric ulcers, duodenal ulcers, gastritis, hyperacidic or medicament-related functional gastropathy, reflux esophagitis, Zollinger-Ellison syndrome, heartburn), which can be caused, for example, by microorganisms (e.g. Helicobacter pylori), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula 1 and their pharmacologically acceptable salts are outstandingly suitable for use in human and veterinary medicine, where they are used, in particular, for the treatment and/or prophylaxis of disorders of the stomach and/or intestine.

A further subject of the invention are therefore the compounds according to the invention for use in the treatment and/or prophylaxis of the abovementioned diseases.

The invention likewise includes the use of the compounds according to the invention for the production of medicaments which are employed for the treatment and/or prophylaxis of the abovementioned diseases.

The invention furthermore includes the use of the compounds according to the invention for the treatment and/or prophylaxis of the abovementioned diseases.

A further subject of the invention are medicaments which comprise one or more compounds of the formula 1 and/or their pharmacologically acceptable salts.

The medicaments are prepared by processes which are known per se and familiar to the person skilled in the art. As medicaments, the pharmacologically active compounds according to the invention (=active compounds) are either employed as such, or preferably in combination with suitable pharmaceutical auxiliaries or excipients in the form of tablets, coated tablets, capsules, suppositories, patches (e.g. as TTS), emulsions, suspensions or solutions, the active compound content advantageously being between 0.1 and 95% and it being possible to obtain a pharmaceutical administration form exactly adapted to the active compound and/or to the desired onset and/or duration of action of action (e.g. a sustained-release form or an enteric form) by means of the appropriate selection of the auxiliaries and excipients.

The auxiliaries and excipients which are suitable for the desired pharmaceutical formulations are known to the person skilled in the art on the basis of his/her expert knowledge. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, if appropriate in the form of several, preferably 1 to 4, individual doses to achieve the desired result. In the case of a parenteral treatment, similar or (in particular in the case of the intravenous administration of the active compounds), as a rule, lower doses can be used. The establishment of the optimal dose and manner of administration of the active compounds necessary in each case can easily be carried out by any person skilled in the art on the basis of his/her expert knowledge.

If the compounds according to the invention and/or their salts are to be used for the treatment of the abovementioned diseases, the pharmaceutical preparations can also contain one or more pharmacologically active constituents of other groups of medicaments, for example: tranquillizers (for example from the group of the benzodiazepines, for example diazepam), spasmolytics (for example, bietamiverine or camylofine), anticholinergics (for example, oxyphencyclimine or phencarbamide), local anesthetics, (for example, tetracaine or procaine), and, if appropriate, also enzymes, vitamins or amino acids.

To be emphasized in this connection is in particular the combination of the compounds according to the invention with pharmaceuticals which inhibit acid secretion, such as, for example, $H_2$ blockers (e.g. cimetidine, ranitidine); $H^+/K^+$ ATPase inhibitors (e.g. omeprazole, pantoprazole), or further with so-called peripheral anticholinergics (e.g. pirenzepine, telenzepine) and with gastrin antagonists with the aim of increasing the principal action in an additive or super-additive sense and/or of eliminating or of decreasing the side effects, or further the combination with antibacterially active substances (such as, for example, cephalosporins, tetracyclines, penicillins, macrolides, nitroimidazoles or alternatively bismuth salts) for the control of Helicobacter pylori. Suitable antibacterial co-components which may be mentioned are, for example, meziocillin, ampicillin, amoxicillin, cefalothin, cefoxitin, cefotaxime, imipenem, gentamycin, amikacin, erythromycin, ciprofloxacin, metronidazole, clarithromycin, azithromycin and combinations thereof (for example clarithromycin+metronidazole).

Pharmacology

The excellent gastric protective action and the gastric acid secretion-inhibiting action of the compounds according to the invention can be demonstrated in investigations on animal experimental models. The compounds according to the invention investigated in the model mentioned below have been provided with numbers which correspond to the numbers of these compounds in the examples.

Testing of the Secretion-inhibiting Action on the Perfused Rat Stomach

In Table A which follows, the influence of the compounds according to the invention on the pentagastrin-stimulated acid secretion of the perfused rat stomach after intravenous administration in vivo is shown.

TABLE A

| No. | Dose (µmol/kg) i.v. | Inhibition of acid secretion (%) |
|---|---|---|
| 17 | 3 | 100 |

Methodology

The abdomen of anesthetized rats (CD rat, female, 200–250 g; 1.5 g/kg i.m. urethane) was opened after tracheotomy by a median upper abdominal incision and a PVC catheter was fixed transorally in the esophagus and another via the pylorus such that the ends of the tube just projected into the gastric lumen. The catheter leading from the pylorus led outward into the right abdominal wall through a side opening.

After thorough rinsing (about 50–100 ml), warm (37° C.) physiological NaCl solution was continuously passed through the stomach (0.5 ml/min, pH 6.8–6.9; Braun-Unita 1). The pH (pH meter 632, glass electrode EA 147; φ=5 mm, Metrohm) and, by titration with a freshly prepared 0.01N NaOH solution to pH 7 (Dosimat 665 Metrohm), the secreted HCl were determined in the effluent in each case collected at an interval of 15 minutes.

The gastric secretion was stimulated by continuous infusion of 1 µg/kg (=1.65 ml/h) of i.v. pentagastrin (left femoral vein) about 30 min after the end of the operation (i.e. after determination of 2 preliminary fractions). The substances to be tested were administered intravenously in a 1 ml/kg liquid volume 60 min after the start of the continuous pentagastrin infusion.

The body temperature of the animals was kept at a constant 37.8–38° C. by infrared irradiation and heat pads (automatic, stepless control by means of a rectal temperature sensor).

What is claimed is:
1. A compound of formula 1

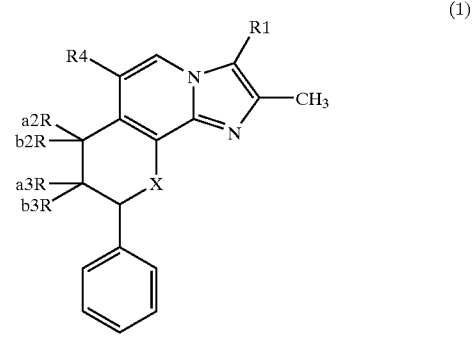

in which

R1 is methyl or hydroxymethyl, one of the substituents R2a and R2b is hydrogen and the other is hydroxyl, methoxy, ethoxy, propoxy, isopropoxy, butoxy, methoxyethoxy or methoxypropoxy, one of the substituents R3a and R3b is hydrogen and the other is hydrogen, hydroxyl, methoxy, ethoxy, propoxy, isopropoxy, butoxy, methoxyethoxy or methoxypropoxy, R4 is carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR5R6, where R5 is hydrogen, 1–7C-alkyl, hydroxy-1–4C-alkyl or 1–4C-alkoxy-1–4C-alkyl and R6 is hydrogen, 1–7C-alkyl, hydroxy-1–4C-alkyl or 1–4C-alkoxy-1–4C-alkyl, or where R5 and R6 together with the nitrogen atom to which both are attached are a pyrrolidino, piperidino or morpholino radical, X is O (oxygen) or NH, or a salt thereof.

2. A compound as claimed in claim 1, of the formula 1*

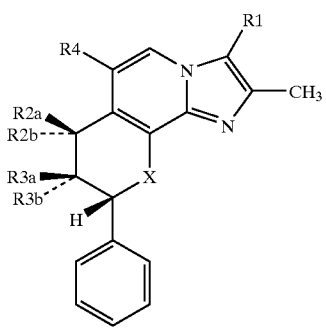

in which

R1 is methyl or hydroxymethyl, one of the substituents R2a and R2b is hydrogen and the other is hydroxyl, methoxy, ethoxy, propoxy, isopropoxy, butoxy, methoxyethoxy or methoxypropoxy, one of the substituents R3a and R3b is hydrogen and the other is hydrogen, hydroxyl, methoxy, ethoxy, propoxy, isopropoxy, butoxy, methoxyethoxy or methoxypropoxy, R4 is carboxyl, —CO-1–4C-alkoxy, hydroxy-1–4C-alkyl, 1–4C-alkoxy-1–4C-alkyl, 1–4C-alkoxy-1C-alkoxy-1–4C-alkyl, fluoro-1–4C-alkoxy-1–4C-alkyl or the radical —CO—NR5R6, where R5 is hydrogen, 1–7C-alkyl, hydroxy-1–4C-alkyl or 1–4C-alkoxy-1–4C-alkyl and R6 is hydrogen, 1–7C-alkyl, hydroxy-1–4C-alkyl or 1–4C-alkoxy-1–4C-alkyl, or where R5 and R6 together with the nitrogen atom to which both are attached are a pyrrolidino, piperidino or morpholino radical, X is O (oxygen) or NH, or a salt thereof.

3. A compound of the formula 1* as claimed in claim 2, in which

R1 is methyl, one of the substituents R2a and R2b is hydrogen and the other is methoxy, ethoxy, propoxy, isopropoxy, butoxy, methoxyethoxy or methoxypropoxy, one of the substituents R3a and R3b is hydrogen and the other is hydrogen or hydroxyl, R4 is hydroxymethyl, methoxymethyl, methoxyethoxymethyl, difluoromethoxymethyl or the radical —CO—NR5R6, where R5 is hydrogen, methyl, ethyl, propyl, 2-hydroxyethyl or 2-methoxyethyl and R6 is hydrogen, methyl or ethyl, X is O (oxygen) or NH, or a salt thereof.

4. A compound of the formula 1* as claimed in claim 2, in which

R1 is methyl, one of the substituents R2a and R2b is hydrogen and the other is hydroxyl, methoxy, ethoxy, propoxy, isopropoxy, butoxy, methoxyethoxy or methoxypropoxy, R3a is hydroxyl, R3b is hydrogen, R4 is 1–4C-alkoxy-1–4C-alkyl, X is O (oxygen) or NH, or a salt thereof.

5. A compound of the formula 1* as claimed in claim 2, in which

R1 is methyl, one of the substituents R2a and R2b is hydrogen and the other is methoxy, ethoxy, propoxy, isopropoxy, butoxy, methoxyethoxy or methoxypropoxy, R3a is hydroxyl, R3b is hydrogen, R4 is methoxymethyl, X is NH, or a salt thereof.

6. A compound as claimed in claim 3 in which R4 is hydroxymethyl, methoxymethyl, methoxyethoxymethyl or difluoromethoxymethyl.

7. A medicament comprising a compound as claimed in claim 1 and/or a pharmacologically acceptable salt thereof together with customary pharmaceutical auxiliaries and/or excipients.

8. A method of preventing or treating gastrointestinal diseases in a patient comprising administering to a patient in need thereof a therapeutically effective amount of a compound as claimed in claim 1 or a pharmaceutically acceptable salt thereof.

* * * * *

UNITED STATES PATENT AND TRADEMARK OFFICE
CERTIFICATE OF CORRECTION

PATENT NO. : 6,696,461 B2
DATED : February 24, 2004
INVENTOR(S) : Senn-Bilfinger et al.

It is certified that error appears in the above-identified patent and that said Letters Patent is hereby corrected as shown below:

<u>Column 23,</u>
Lines 44-45, change "1-4C-alkoxy-1-C-alkoxy-1-4C-alkyl" to -- 1-4C-alkoxy-1-4C-alkoxy-1-4C-alkyl --.

Signed and Sealed this

Fifteenth Day of June, 2004

JON W. DUDAS
*Acting Director of the United States Patent and Trademark Office*